United States Patent [19]

Noren

[11] 4,044,054

[45] Aug. 23, 1977

[54] 2-OXO-3-ALKENYL DIMETHYLAMINE

[75] Inventor: Gerry Karl Noren, Hoffman Estates, Ill.

[73] Assignee: Calgon Corporation, Pittsburgh, Pa.

[21] Appl. No.: 675,379

[22] Filed: Apr. 9, 1976

[51] Int. Cl.$^2$ .............................................. C07C 97/03
[52] U.S. Cl. .......................... 260/584 A; 260/63 UY; 260/79.3 R; 260/79.3 MU; 526/291
[58] Field of Search ......... 260/584 A, 583 H, 63 UY; 526/291

[56] References Cited

FOREIGN PATENT DOCUMENTS

| 2,223,241 | 11/1973 | Germany | 260/584 A |
| 74-45307 | 12/1974 | Japan | 260/584 A |

Primary Examiner—Daniel E. Wyman
Assistant Examiner—John J. Doll
Attorney, Agent, or Firm—Rudolph J. Anderson, Jr.; Harry E. Westlake, Jr.; Martin L. Katz

[57] ABSTRACT (2-oxo-3-butenyl)dimethylamine monomers which may be used in the preparation of high molecular weight water-soluble cationic polymers which may be used as flocculants, drainage and retention aids, or conductive polymers.

2 Claims, No Drawings

2-OXO-3-ALKENYL DIMETHYLAMINE

This invention relates to new cationic monomers which may be used in the preparation of high molecular weight water-soluble polymers.

More particularly, this invention relates to the preparation of new cationic monomers which have a low mass to charge ratio, the ability to copolymerize with other vinyl monomers and satisfactory economics.

These and other criteria are satisfied by monomers of the formula:

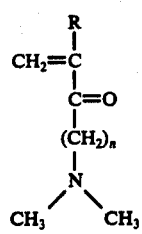

I.

wherein:
R may be hydrogen or methyl; and
n may be 1 to 3.

Upon quaternization and polymerization, monomers of Formula I result in polymers having repeating units of the formula:

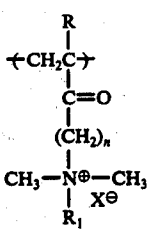

II.

wherein:
R and n are as defined above;
$R_1$ may be alkyl (1-4 carbon), hydroxyalkyl (1-4 carbon), benzyl or allyl; and
X may be halogen or methyl sulfate.

The preferred members of this class are (2-oxo-3-butenyl) dimethylamine and polymers thereof.

The compounds of this invention may be prepared by a process which consists of the condensation of a halogen substituted alkyl vinyl ketone such as chloromethyl vinyl ketone with cyclopentadiene in a Diels-Alder reaction. This initial step is necessary to protect the vinyl group during the ensuing nucleophilic substitution reaction. The product of the Diels-Alder reaction can now be reacted with a nucleophilic agent such as dimethylamine to replace the reactive halogen. This product containing the tert-amino functionality can now be thermally decomposed in a Retro-Diels-Alder reaction to reform the vinyl group and give a tert-amino substituted alkyl vinyl ketone. Reaction with an alkylating agent results in the quaternization and subsequent polymerization to the desired quaternary ammonium substituted polymer. Alternatively, the methyl sulfate quaternary compound and resulting polymer may be formed. This process is represented by the following reaction scheme:

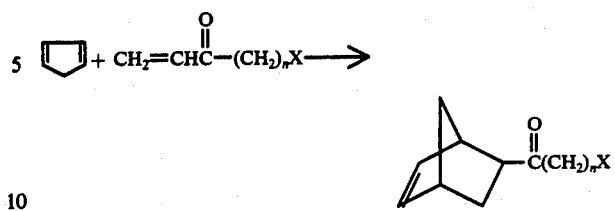

A.

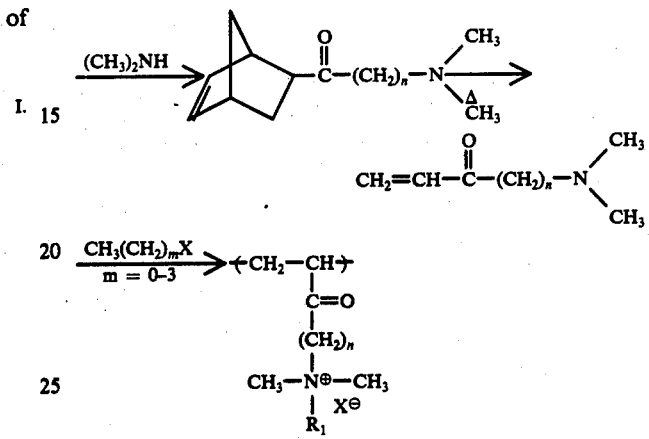

Alternatively, the following processes may be used to prepare the compounds of this invention which can be polymerized in conventional manners well-known to those having ordinary skill in the art. Process B can be converted to process C after step 2 by quaternization with the appropriate alkyl halide, thereby forming the quaternary ammonium salt before cleavage of the carboxyl function.

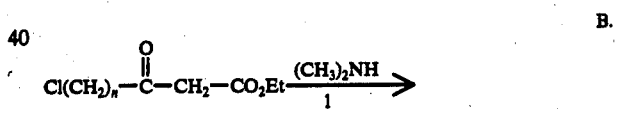

B.

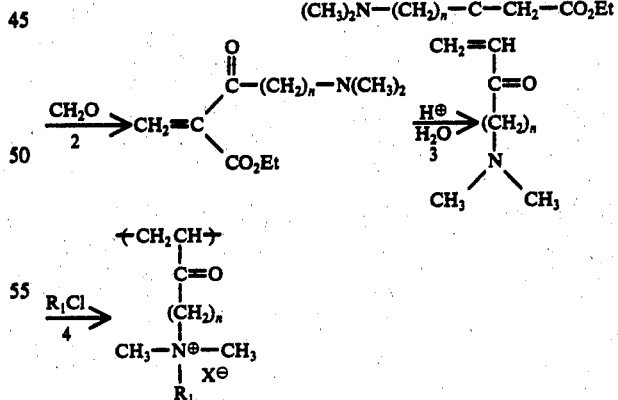

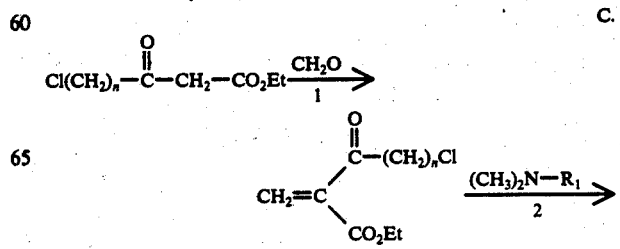

C.

-continued

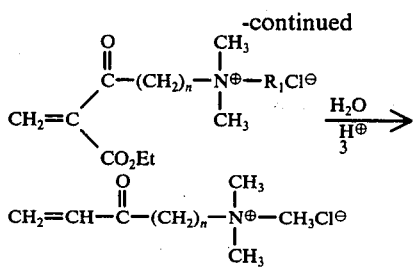

The monomers of this invention may be used to prepare cationic polymers which may be used as flocculants, drainage and retention aids or conductive polymers in manners well-known to those having ordinary skill in the art.

This preparation of monomers and polymers of this invention may be illustrated by the following examples.

EXAMPLE 1

5-Chloroacetyl-2-Norbornene

Cyclopentadiene (10 g; 12.5 ml; 0.152 mole) was added slowly over a 20 min. period to 10 g (0.096 mole) of chloromethyl vinyl ketone. The reaction was slightly exothermic and some cooling was required. After the reaction had stirred at room temperature for 30 min., it was heated to reflux for an additional 60 min. Distillation of the crude product gave three fractions. The fraction boiling at 105°–107°/4.5 mm was 5-chloroacetyl-2-norbornene.

EXAMPLE 2

5-Dimethylaminoacetyl-2-Norbornene

To a solution of 3.5 g (5.2 ml; 0.078 mole) of dimethylamine in 40 ml of ether at -15° was added 6.5 g (0.038 mole) of 5-chloroacetyl-2-norbornene. The reaction mixture was stirred for 7 hr. at 0° (ice bath) and then allowed to warm to room temperature overnight. The solid dimethylamine hydrochloride was removed by filtration and the ether was removed at reduced pressure to give 6.1 g (89%) of crude product. Distillation gave product bp 83°–90°/0.8 mm.

EXAMPLE 3

Quaternization of 5-Dimethylaminoacetyl-2-Norbornene

Methyl chloride gas was bubbled through a solution of 0.5 ml of 5-dimethylaminoacetyl-2-norbornene in 1 ml of benzene for 45 min. The mixture was allowed to sit overnight and the solid isolated by filtration. A nearly quantitative yield was obtained.

EXAMPLE 4

5-Carbomethoxy-2-Norbornene

Cyclopentadiene (16g; 20 ml; 0.24 mole) was added slowly to 15.2 g (0.177 mole) of methyl acrylate at room temperature. The reaction was allowed to stir over the weekend. The excess cyclopentadiene was removed at reduced pressure and the product was distilled (bp 45°–49°/1.7 mm) to give 21 g (78%) of 5-carbomethoxy-2-norbornene.

EXAMPLE 5

5-(4-Dimethylaminobutyryl)-2-Norbornene

A solution of 3-dimethylaminopropylmagnesium chloride was prepared from 8 g (0.066 mole) of 3-dimethylaminopropylchloride and 1.5 g (0.062 g-atom) of magnesium in 50 ml of dry tetrahydrofuran. The Grignard reagent was added to 10 g (0.066 mole) of 5-carbomethoxy-2-norbornene for 5 hr., cooled, and hydrolyzed on a mixture of 100 ml of 10% hydrochloric acid and 50 g of ice. The unreacted 5-carbomethoxy-2-norbornene was extracted with ether. Then the mixture was neutralized with 50% potassium hydroxide and extracted with ether. The ether extracts were dried over anhydrous magnesium sulfate and distilled. The fraction boiling at 106°–120°/1.2 mm was collected. Yield 2 g (16.5%).

EXAMPLE 6

3-Dimethylaminopropyl Vinyl Ketone

The 5-(4-dimethylaminobutyryl)-2-norbornene (2 g; 0.001 mole) was pyrolyzed at 490° and 1 mm to give crude 3-dimethylaminopropyl vinyl ketone.

EXAMPLE 7

5-Chloroacetyl-2-Norbornene

A solution of 8.8 g (0.11 mole) of sodium acetate and 9.9 g (0.15 mole) of cyclopentadiene in 40 ml of 95% ethanol was cooled to 0° in an ice bath and then 14.4 g (0.102 mole) of 1,4-dichloro-2-butanone was added. After 20 hr. at room temperature, a gas chromatogram showed that the product had formed. The ethanol was removed at reduced pressure and the residue distilled to give 6.5 g (38%) of product 6 p 78°/2 mm.

The 5-chloroacetyl-2-norbornene produced in Example 7 may be reacted by the procedures of Examples 2 and 3.

EXAMPLE 8

Quaternization-Polymerization of 3-Dimethylaminopropyl Vinyl Ketone 3-dimethylaminopropyl vinyl ketone (1 g) was dissolved in 1 ml of acetone and methyl chloride gas was bubbled through the solution for 15 min. at room temperature. The resultant solution was allowed to stir for 24 hr. at room temperature at which time a while solid mass had formed. The while solid was isolated by filtration and dried. A qualitative test for chloride ion using silver nitrate was positive. The nmr spectrum showed the presence of protons on a methyl of a quaternary nitrogen and the presence of aliphatic protons. No vinyl proton absorptions were present.

I claim:

1. A compound of the formula

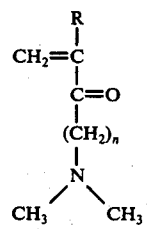

wherein:
R may be hydrogen or methyl; and
$n$ may be 1 to 3.

2. A compound as in claim 1 where R is hydrogen and $n$ is 1.

* * * * *